United States Patent
Smirniotopoulos et al.

(10) Patent No.: US 7,080,098 B2
(45) Date of Patent: Jul. 18, 2006

(54) MEDICAL MULTIMEDIA DATABASE SYSTEM

(76) Inventors: James G. Smirniotopoulos, 204 Eldrid Dr., Silver Spring, MD (US) 20904; Henry Andrew Irvine, 7211 Hilton Ave., Takoma Park, MD (US) 20912

( * ) Notice: Subject to any disclaimer, the term of this patent is extended or adjusted under 35 U.S.C. 154(b) by 790 days.

(21) Appl. No.: 10/138,793

(22) Filed: May 2, 2002

(65) Prior Publication Data

US 2003/0208477 A1 Nov. 6, 2003

(51) Int. Cl.
G06F 7/00 (2006.01)

(52) U.S. Cl. .................. 707/104.1; 707/100; 707/101; 707/102

(58) Field of Classification Search ......... 707/1–104.1; 705/1–3, 50–53, 14, 57, 80, 26–27; 711/117–118, 711/100; 235/492, 487; 345/764, 853; 715/501.1; 709/200, 204, 217–219; 713/200–201; 725/139–142
See application file for complete search history.

(56) References Cited

U.S. PATENT DOCUMENTS

| | | | |
|---|---|---|---|
| 5,325,294 A | 6/1994 | Keene | |
| 5,974,389 A | 10/1999 | Clark et al. | |
| 5,991,731 A | 11/1999 | Colon et al. | |
| 6,073,106 A | 6/2000 | Rozen et al. | |
| 6,182,047 B1 | 1/2001 | Dirbas | |
| 6,234,964 B1 * | 5/2001 | Iliff | 600/300 |
| 6,272,470 B1 * | 8/2001 | Teshima | 705/3 |
| 6,466,941 B1 * | 10/2002 | Rowe et al. | 707/102 |
| 6,609,135 B1 * | 8/2003 | Omori et al. | 707/104.1 |
| 2001/0032100 A1 | 10/2001 | Mahmud et al. | |
| 2001/0041991 A1 | 11/2001 | Segal et al. | |
| 2002/0026332 A1 | 2/2002 | Snowden et al. | |
| 2002/0029157 A1 | 3/2002 | Marchosky | |

OTHER PUBLICATIONS

JG Smirniotopoulos and H. Irvine, "Instructions for Using MedPix", Oct. 25, 2000, pp. 1-38.*
MedPix Website—archived as of Oct. 25, 2000, pp. 1-38.

* cited by examiner

Primary Examiner—Luke S Wassum
Assistant Examiner—Linh Black
(74) Attorney, Agent, or Firm—John P. Moran

(57) ABSTRACT

A medical image storage and retrieval system includes a database with relationally linked tables including a disease factoid table, an image and image caption table, and a patient data table. A flexible system allows for peer review, remote access and maintenance of the stored data, and query searching and retrieval of groups of related multimedia (image and text) case file information. The system facilitates distance learning and remote consultation.

18 Claims, 21 Drawing Sheets

| Review ALL – Patients – Captions – Images – Factoids – Authors ‖ EDIT |
| Browse Mode ▼ ‖ Search   Review My ▼ ‖ Registration  Sign *In* / Out ‖ Build |
| Previous Screen   No Frames ‖ Main Menu   Print Page   Help? |

Case Builder:
Create a MedPix™ Teaching File Case

NOTE
You May Create a New Factoid – or – Choose an Existing Factoid with [Search Factoids]
From any page, Click [Build Case] to return here.
To Finish and Quit, Choose [Close Case]

Begin New MedPix™ Case

| Step | Process | Action |
|---|---|---|
| ⇨Begin>>> | Step 1 | Disease Factoid: Create ‖ Select ‖ My Own [Search] |
| Step 2 | Patient Profile Data: | |
| Step 3 | Create Caption/Upload Image: | |
| Step 4 | Add More Images – Use ==> | |
| I'm Done | Close This Case | |
| | | You may always come back later and edit your work |

[Please Read These Instructions]

Manual Creation Mode
(This Will NOT Create Links)

[Add New Factoid] [Add New Image] [Add New Patient]

Free Online Spell Check:

[Spell Check Window]

FIG. 4

| Review ALL - Patients - Captions - Images - Factoids - Authors ‖ EDIT |
| Browse Mode ▼ ‖ Search   Review My ▼ ‖ Registration  Sign *In* / Out ‖ Build |
| Previous Screen    No Frames ‖ Main Menu   Print Page   Help? |

  Search MedPix™ for:

- Disease Factoids
- Factoids by ACR Code
- Images/Captions [X-ray]
- Images by ACR Code
- Search Patients by Age
- Glossary
- Mnemonics
- Selective Search

- 
- 
- 
- 
- 
- 
- 
-

▲ Back to Top ▲

Go to Search Factoids

FIG. 5A

| Search MedPix™ Images |
| --- |
| RADIOLOGY - Click Here to Search by ACR Code |
| Images by Plane (only) ○     Images by Plane (only) ○<br>Image Plane: [Plane ▼]    [Select From Menu ▼]<br>◉ Match Both Plane AND Modality    Limit Display to [5 ▼] Images/Captions |
| HINT: Join words with a '+' to make a phrase.<br>(Example: Using 'brain + tumor' will find the exact phrase 'brain tumor'. But, 'brain [space] tumor' is different — you'll be searching for two separate words: 'brain' OR 'tumor' or 'brain' AND 'tumor' depending on the type of search.) |
| Search Image Library by Caption Text (Registered Users Only)<br>Look for: [       ]    [Search Captions]<br>○ OR - may have any one (or more) of the Words or Phrases<br>◉ AND - must include ALL of the Words & Phrases |

- 
- 
- 
- 
- 
- 
-

▲ Back to Top ▲
Go to Search Images

| Search MedPix™ Disease Factoids |
| --- |
| Radiology Cases - Click Here to Search by ACR Code |
| Search by Organ System/Location    Search by Disease Category<br>○ [Select From Menu and Check Box ▼]    ○ [Select From Menu and Check Box ▼]<br>◉ Match BOTH Location AND Category    Limit [5 ▼] Abstracts per Page. [Fetch Factoids] |

FIG. 5B

| Search Disease Factoids (Titles Only) |
| --- |
| Looking for: [          ]  [Search Topics] |

HINT: Join words with a '+' to make a phrase.
(Example: Using 'brain + tumor' will find the exact phrase 'brain tumor'. But, 'brain [space] tumor' is different — you'll be searching for two separate words: 'brain' OR 'tumor' or 'brain' AND 'tumor' depending on the type of search.)

Search Disease Factoids (Full Text)

Looking for: [          ]  [Search Text]

○ OR - may have any one (or more) of the Words or Phrases
◉ AND - must include ALL of the Words & Phrases
◉ List All Matching Factoids  ||  ○ [X-ray] - Only Factoids with Pictures EDITOR'S Search  ○ Submissions Bin Only - or -  ○ Main Database Only
                                                                          (Default)
Limit [10 ▼] Factoids per Page Search by Edit/Modification Date:  [Submit Query]
◉ 1 day  ○ 3 days  ○ 1 week  ○ 1 month  ○ 2 months  ○ 3 months Search by Submission/Creation Date:  [Submit Query]
○ 1 day  ○ 3 days  ◉ 1 week  ○ 1 month  ○ 2 months  ○ 3 months Search for Text as a Keyword (only)
Looking for: [          ]  [Search Keywords]

Selective (Boolean) Search

△ Back to Top △

Review ALL - Patients - Captions - Images - Factoids - Authors || EDIT
[Browse Mode ▼] || Search  [Review My ▼] || Registration  Sign *In* / Out || Build
            [Previous Screen]  No Frames || Main Menu  [Print Page]  [Help?]

Click HERE to vote for this page as a Starting Point Hot Site.

Portions of this Program and the Content Images and Text are Copyright © 1999-2001 by the original content Contributors and/ or by H Irvine and JG Smirniotopoulos, M.D.

MedPix™ Has Displayed [X][X][X][X][X][X][X] pages since 3 September 2000.

FIG. 5C

MedPix™ Patient Browser
(Choose Options Below)

Options - History: Yes ○ No ● | Thumbnail: Yes ○ No ●

Display [10 ▼] Patients/Page. [Go!]

10 Patient Profiles  (1-10 ID sorted descending)  [Next 10]

| Pt ID: 4403 | This woman is 18. | View as Quiz | Case Discussion |
| Pt ID: 4402 | This caucasian patient is 51. | View as Quiz | Case Discussion |
| Pt ID: 4401 | This woman is 41. | View as Quiz | Case Discussion |
| Pt ID: 4400 | This woman is 17. | View as Quiz | Case Discussion |
| Pt ID: 4395 | This man is 51. | View as Quiz | Case Discussion |
| Pt ID: 4394 | This woman is 20. | View as Quiz | Case Discussion |
| Pt ID: 4393 | This woman is 19. | View as Quiz | Case Discussion |
| Pt ID: 4391 | This patient is 25. | View as Quiz | Case Discussion |
| Pt ID: 4390 | This Polynesian Woman is 46. | View as Quiz | Case Discussion |
| Pt ID: 4386 | This woman is 60. | View as Quiz | Case Discussion |

| ID= 9568 | ID= 9569 |
|---|---|
| Radiation Accident at an Industrial Accelerator Facility... | Radiation Accident at an Industrial Accelerator Facility... |
| [ Edit Image ] | [ Edit Image ] |

| Note: Images and Text © by the Contributor, JGS and/or others – 1999, 2001 Please be academically honest – request permission and provide attribution when using this material. | Card Factoid 3424 |
|---|---|
| Reference(s): Schauer, et. al., Health Physics, 65, 131–140 (1993) – Cover Article | |
| Related Web Site: JUMP to Related LINK | |
| Factoid 3424 Prepared or Submitted by: David A Schauer  View Author Info Uniformed Services University | ☒ |
| Peer Review/Acceptance: James G. Smirniotopoulos, M.D.    View Editor List | |

This Factoid does not have any comments.
To add comments and/or review, click on [Review] below.

---

Add Your Comments and/or a Review  [ Review Window ]  [ Review Here ] — 807
Add an Image to this Factoid  [ Add Image ]

Review ALL – Patients – Captions – Images – Factoids – Authors || EDIT
[ Browse Mode ▼ ] || Search  [ Review My ▼ ] || Registration  Sign *In* / Out || Build
[ Previous Screen ]   No Frames || Main Menu   [ Print Page ]   [ Help? ]

FIG. 8B

15 Search Results (ID sorted descending) [Next 15]

15 Factoids Matching Your Search Criteria (Use Prev/Next to See More):

| Images | ACR Code | Author | Factoid | Factoid Title |
|---|---|---|---|---|
| ⊙ | 2:5 | 2 | VIEW EDIT | Thyrotoxicosis Epidemic |
| Xray | 2:5 | 561 | VIEW EDIT | DeQuervain's Thyroiditis |
| Xray | 9:1 | 901 232 | VIEW EDIT | Adrenal Gland |
| ⊙ | 2:3 | 730 | VIEW EDIT | Papillary Thyroid Carcinoma |
| ⊙ | 1:-1 | 2 | VIEW EDIT | Diabetes Insipidus |
| ⊙ | 1:5 | 110 | VIEW EDIT | Hypernatremia (causes) |
| Xray | 2:3 | 5 | VIEW EDIT | Parathyroid Adenoma |
| Xray | 1:3 | 2 | VIEW EDIT | Goliath, Did he have Acromegaly/Gigantism |
| Xray | 2:2 | 588 | VIEW EDIT | Subacute Thyroiditis |
| Xray | 86 544 | 681 | VIEW EDIT | Primary Aldosteronism |
| Xray | 2:8 | 5 | VIEW EDIT | Papillary Carcinoma of the Thyroid |
| Xray | 2:8 | 5 | VIEW EDIT | Hashimoto's Thyroiditis |
| Xray | 1:8 | 5 | VIEW EDIT | Adrenal Cortical Adenoma |
| Xray | 1:8 | 5 | VIEW EDIT | Neuroblastoma |
| Xray | 1:7 | 5 | VIEW EDIT | Pheochromoctoma |

FIG. 9A

Review ALL – Patients – Captions – Images – Factoids – Authors || EDIT
Browse Mode ▼ || Search   Review My ▼ || Registration   Sign *In* / Out || Build
Previous Screen   No Frames || Main Menu   Print Page   Help?

MedPix™
Medical Images, Factoids, and Mnemonics.
Click Here to Browse by ACR Location

Browse by MedPix™ Location

Click on a Location Heading to see topics relevant to that Location.
or Go Back to the Main Menu Location or Organ System ▼ | Select Browse Mode Browsing Factoids by Anatomic Location If a folder fails to open or close - Please Reload/Refresh your browser -
or Click Here!
Purge Expando State and
List = Array and Source = geography and Expand=82 and Collapse=

- ☒ expand  Abdomen - Generalized
- ☒ expand  Brain and Meuro
- ☒ expand  Breast
- ☒ expand  Cardiovascular (inc. Heart)
- ☒ expand  Chest, Pulmonary (ex. Heart)
- ☒ expand  Dermatology
- ☒ expand  Endocrine (clinical)
- ☒ expand  Eye and Orbit
- ☒ expand  Gastrointestinal
- ☒ expand  Generalized
- ☒ expand  Genitourinary
- ☒ expand  Head and Neck (ex. orbit)

FIG. 11A

- ☒ expand  Hematopoietic
- ☒ expand  Miscellaneous
- ☒ expand  Multisystem

- ☒ expand  Angiogenesis
    - ☒ expand  Billions of Cells
    - ☒ expand  Carney Syndrome
    - ☒ expand  Germ Cell Tumors
    - ☒ expand  MELAS
    - ☒ expand  Metastatic Transitional Cell Carcinoma to the Esophagus
    - ☒ expand  Normal Chest and Abdomen - Angiograms
    - ☒ expand  Radiation Accident at an Industrial Accelerator Facility
    - ☒ expand  Smallpox
    - ☒ expand  Tinnitus
    - ☒ expand  Tuberous Sclerosis, diagnostic criteria
    - ☒ expand  tumor template
    - ☒ expand  tumor template
    - ☒ expand  von Hippel - Lindau Disease

- ☒ expand  Musculoskeletal
- ☒ expand  Nerve, central
- ☒ expand  Nerve, peripheral
- ☒ expand  Pathology

FIG. 11B

| Review ALL – Patients – Captions – Images – Factoids – Authors ‖ EDIT |
|---|
| Browse Mode ▼ ‖ Search    Review My ▼ ‖ Registration   Sign *In* / Out ‖ Build |
| Previous Screen    No Frames ‖ Main Menu    Print Page    Help? |

| Edit Window | —[EDIT Here] | Add an Image |
|---|---|---|

Build Case W/ 2733

Angiogenesis (Created: 2001-09-01 19:39:24-04)(Last modified: 2001-09-03 07:27:34-04)

Location: Multisystem    Sublocation: None Selected    Category: Physiology Find Related Topics: Click on the [X], Location, or the Category above.

Angiogenesis is a key ingredient in the success of tumors. Solid tumors cannot grow larger than 1-3 mm3 in size without creating new vessels. One of the pioneers in studying angiogenesis (and in proposing anti-angiogenesis as a treatment) is Dr. Judah Folkman. In the 1970's he began to study how tumors stimulate the growth of vessels.

For the average (70kg) person
  1,000,000,000,000 endothelial cells
  Total Endothelial Surface Area - 1000 m2 - roughly the size of a tennis court Tumors < 500 microns are able to survive by diffusion
  Tumors > 1-2 mm w/o neovascularity stop dividing and have apoptosis Angiogenesis on the Web:
  http://www.med.unibs.is/~airc/
  (This is where the images came from, courtesy of Prof. Marco Presta).

http://zygote.swarthmore.edu/mesend3b.html http://rex.ncl.nih.gov/massmedia/backgrounders/angio.htm http://primarycare.medscape.com/thieme/SRE/1999/v17.n03/sre1703.02.murr/sre1703.02.murr-05.html Commerical Website:
http://www.angloworld.com/cancer.htm Image    Image    Image

FIG. 11C

| ID=8724 | ID=8725 | ID=8726 |
| :---: | :---: | :---: |
| Angiogenesis | Angiogenesis | Angiogenesis |
| [ EDIT Window ] | [ EDIT Window ] | [ EDIT Window ] |

| Note: Images and Text © by the Contributor, JGS and/or others – 1999, 2001 Please be academically honest – request permission and provide attribution when using this material. | Card Factoid 3424 |
| --- | --- |
| Reference(s):<br>Schauer, et. al., Health Physics, 65, 131–140 (1993) – Cover Article | |
| Related Web Site: JUMP to Related LINK | |
| Factoid 3424 Prepared or Submitted by:<br>David A Schauer  View Author Info<br>Uniformed Services University | ☒ |
| Peer Review/Acceptance: James G. Smirniotopoulos, M.D.    View Editor List | |

This Factoid does not have any comments.
To add comments and/or review, click on [Review] below.

Add Your Comments and/or a Review  [ Review Window ]  [ Review Here ]
Add an Image to this Factoid  [Add Image]

Review ALL – Patients – Captions – Images – Factoids – Authors || EDIT
[ Browse Mode ▼ ] || Search  [ Review My ▼ ] || Registration  Sign *In* / Out || Build
[ Previous Screen ]   No Frames || Main Menu  [ Print Page ]  [ Help? ]

FIG. 11D

MEDICAL MULTIMEDIA DATABASE SYSTEM

STATEMENT OF GOVERNMENT RIGHTS

The Government has certain rights in this invention.

FIELD OF THE INVENTION

The invention relates generally to multimedia database systems and in particular to a multimedia database system storing medical images.

BACKGROUND OF THE INVENTION

Over the past decade there has been a dramatic increase in the quality and types of imaging tools available to medical practitioners. There have also been significant advances in our ability to digitally capture and store large data files, and a variety of attempts have been made to apply these new storage technologies to the proliferating volumes of medical images.

However, despite these recent advances there remains a significant gap between a medical practitioner's ability to collect multimedia information, and his or her ability to intelligently and efficiently use this information. In typical applications images are stored as part of a flat-file system, retrievable only when later accessing specific patient information. This amounts to little more than a digital version of the analog file systems of old. Where databases have been employed as something more than just enhanced filing systems, what is typically implemented is simple indexing around a title or specialized code. Many of these systems are also confined to closed networks. Where external access is available, little more than a static display is offered.

All of these approaches leave most of the promise of enhanced information-based productivity for the medical practitioner unfulfilled. There remains, therefore, a need for a system that is robust, interactive, and permits geographically remote practitioners to create, update, and relationally search multimedia medical information.

SUMMARY OF THE INVENTION

These and other problems are solved by the invention described herein. In a present embodiment, a multimedia medical database includes a table space with multiple related tables, at least one of which stores medical images. Thus, for example, in the MedPix™ product implementation of this embodiment, information is relationally stored in separate tables. These tables preferably include a disease information or "factoid" table, an image/caption table, and a patient/clinical data table. Additional tables may also be used, for example, to store user privileges, track student results, and capture expert information for generating specialized files like teaching files. This system can be used via any appropriate networking device, thus allowing for broad access. This permits a fully interactive product for storing, retrieving, and searching against a variety of medically relevant parameters. Since the tables and interfaces are dynamic and the database is relational, a robust information tool is now available to medical professionals anywhere in the world with access to the Internet. Additionally, interactive diagnostic and teaching services may also be provided, allowing multiple physicians to access and discuss multimedia files, and allowing physician's a remote learning or expert platform by which interactive multimedia files may be created and the learning process facilitated via an automated program.

Still other and further aspects, advantages and embodiments of the present invention can be better understood in connection with the following description and by reference to the accompanying drawings.

BRIEF DESCRIPTION OF THE DRAWINGS

FIGS. 3–11D are screen shots illustrating how information may be presented and selected by a user in accordance with the embodiments of FIG. 1 and 2, and in particular:

FIG. 3 illustrates a process for capturing case data;

FIG. 4 illustrates another process for building a new case file;

FIGS. 5A–5C illustrate processes for searching by category, image or factoid information;

FIG. 6 illustrates an implementation for viewing returned image information and for navigating between returned images;

FIGS. 7A–7B illustrate browsing windows for rapidly viewing information;

FIGS. 8A–8B illustrate a returned case file in a format that includes image and factoid information;

FIGS. 9A–9C illustrate another approach to searching, showing the results for a search on physical location information, factoid information in response to a user selection, and image information in response to a further user selection, respectively;

FIGS. 11A–11D illustrate yet another approach to browsing, starting with an expandable glossary of anatomical terms (FIGS. 11A and 11B), and returned medical information for browsing (FIGS. 11C and 11D).

DETAILED DESCRIPTION

Figure 1:
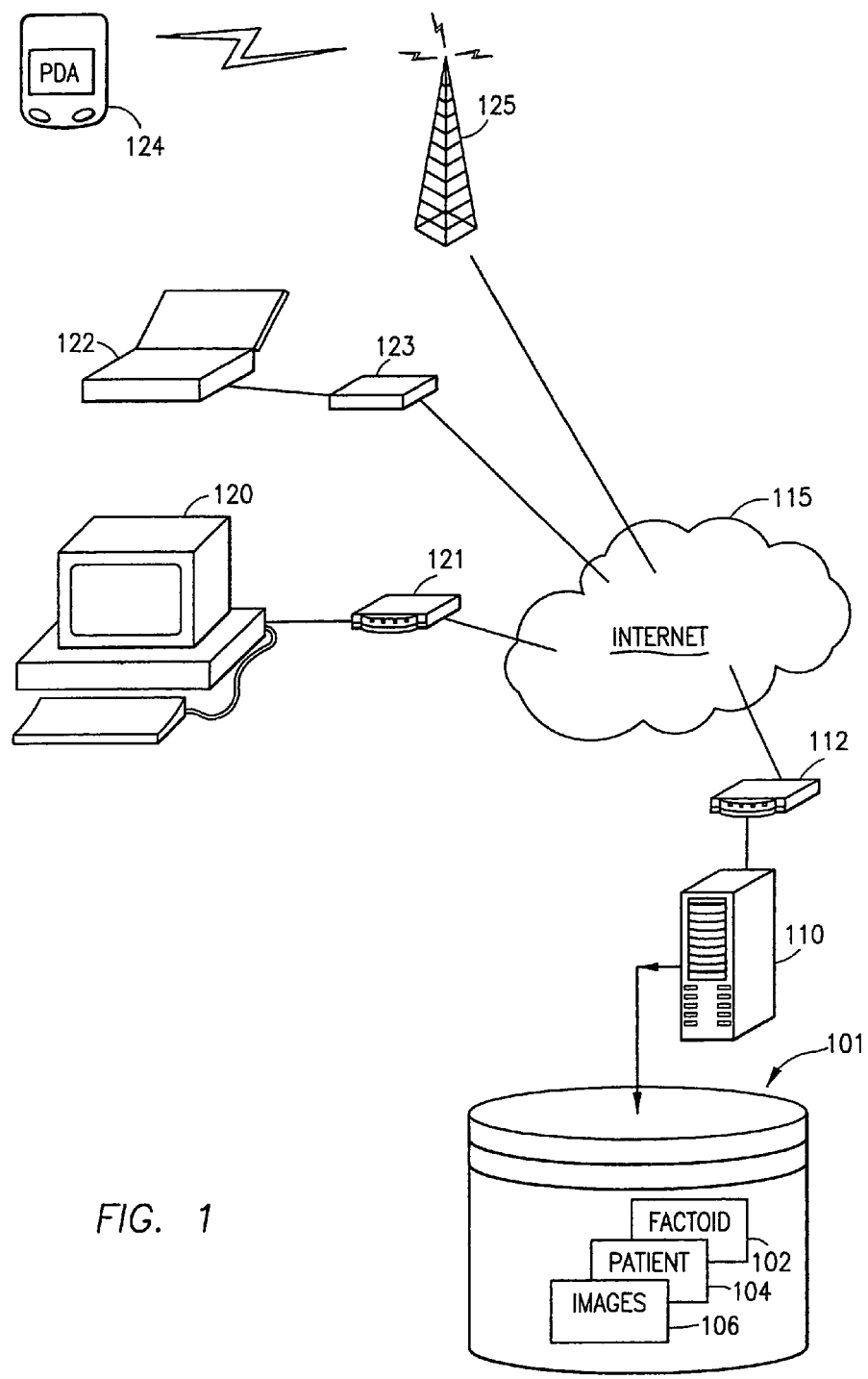
FIG. 1 is a block diagram of an exemplary network-based multimedia medical database system in accordance with the present invention.

Beginning with FIG. 1, a network environment for a multimedia medical database system is illustrated. In this system, a multimedia database 101 stores within its secure table spaces the component tables in which the medical multimedia data is stored. These tables preferably include a disease information or "factoid" table 102, a patient and/or clinical data table 104, and an image and/or caption table 106. These tables are relationally coupled via a program, typically via a DBMS 111 (a "database management system" program), as will be described more fully below, but may otherwise be in any convenient format (including relational, object-oriented, object-relational, etc.). While one implementation of the invention has been developed in PostGres SQL language using HTML, Java script, and PHP v.4 applications running on a LINUX operating system, those skilled in the art will appreciate that the invention may be readily implemented using a variety of database products, programming languages, browser interfaces, operating systems, and hardware platforms, depending on the preference of the developer and characteristics desired for a specific application.

In a current implementation, the multimedia medical database is accessed via a network server 110, which is in turn connected to the Internet 115 via a network router 112. This conveniently allows users to access the database no matter where they are located, as long as they have access to a suitable interface device. When the user is merely accessing the system to view information, the device could be as thin as any hardware and/or software device with a Web-enabled browser, including, e.g., a personal digital assistant 124, a cell phone, or other wireless devices connecting via a wireless infrastructure 125 to the Internet. To make full use of the multimedia database, however, devices such as desktop or laptop computers 120, 122 connected via broadband or dial-up devices 121, 123 can be used. A skilled artisan will appreciate that any one of a variety of devices and configurations could be used in place of those described above. For example, in lieu of server 110 in a client-server architecture, a mainframe, local computer, or any convenient processor and memory combination that is capable of storing the database 101 and accessing/manipulating the table, security and other information, may be used. Similarly, the connection could be via any electromagnetic interface (bridges, infrared links, local and optical networks), not just a router based wide area network, and any convenient input device capable of inputting or outputting via the interface to the database may be used.

Figure 2:
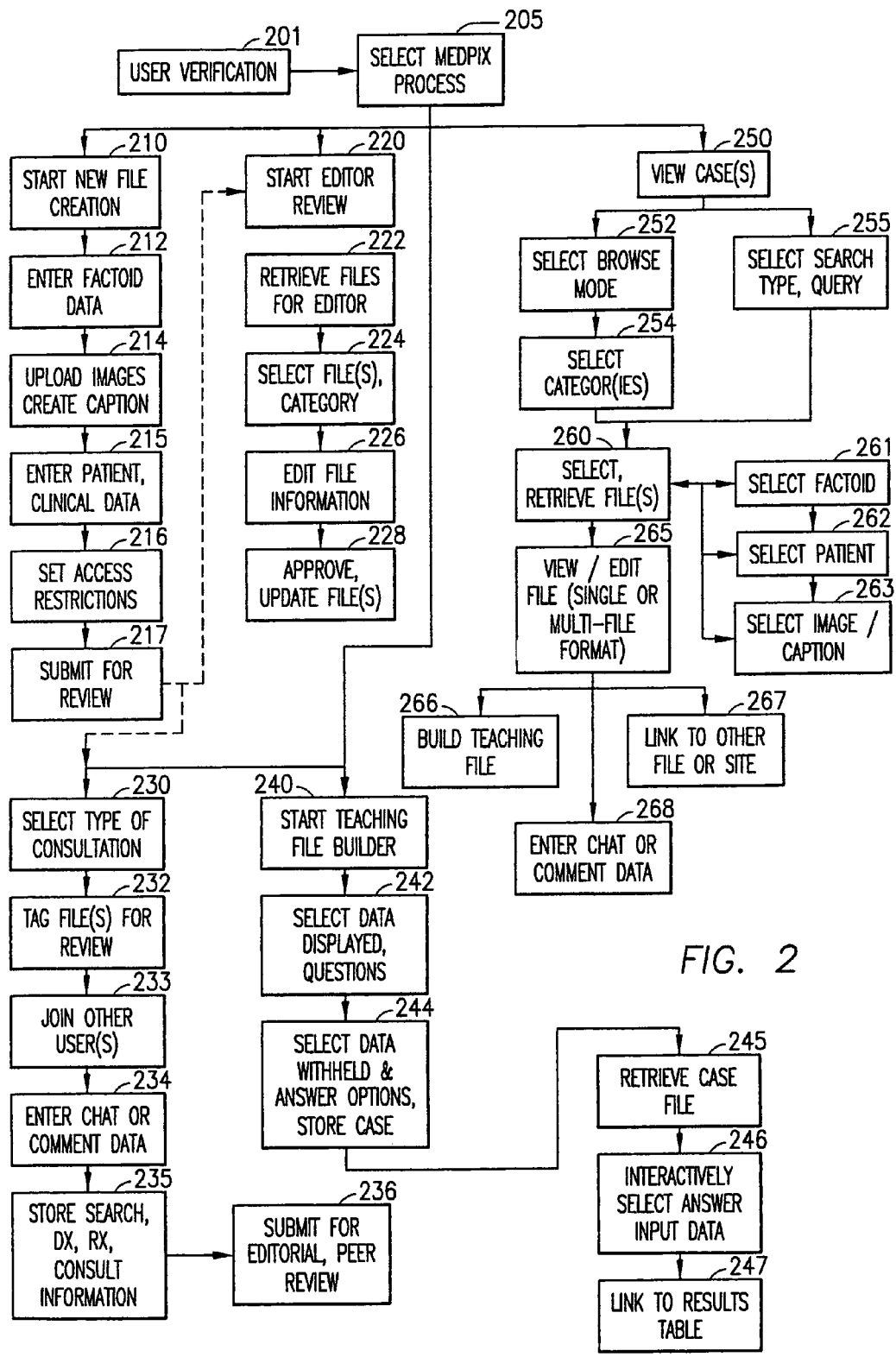
FIG. 2 is a logic flow diagram illustrating exemplary steps employed by a medical multimedia database system in accordance with the present invention.

Turning now to FIG. 2, an overview of the multimedia medical database's functionality is provided from the user's perspective. In the preferred system implementation, the first user step will be an access logon (step 201). This typically includes a user presentation of their system name and a password, although additional levels of security and access control schemes may be used where more sensitive information is being stored. Thus, multiple levels of privileges may be supported, such as for an author of a file, a reviewer, an editor, a guest, and a system administrator. The level of privileges may also vary based upon the state of the file and the particular information being manipulated. For example, where a user with author privileges has the full ability to create a new file, certain fields (such as factoid categories) in the file may still be locked against subsequent changes by the author after the file has been approved by an editor. Similarly, an author may not have privileges to edit modifications like reviewer comments. Moreover, multi-level access control, using role-based or other schemes, may be advantageously employed. Which approach to adopt is a matter of design choice that one skilled in the art would understand how to implement. When using a multi-level system, e.g., the same registered user could be qualified for all five types of privileges, with the particular privilege being determined based upon the file or information within the file that is being accessed. Thus, even though a person acted as both author and editor of a given file, it is possible that after approval he could be restricted to visitor status with respect to certain file access, and may lack even these privileges with respect to portions of the file (e.g., sensitive patient information, where his role has changed vis-à-vis the patient's care). Such versatility can be very handy when dealing with sensitive information, but this must be balanced against the complexity of administering multilevel access.

Once a user is registered with the system, he or she proceeds to select the particular process that they want to use (step 205). For many users, the most common processes will be browsing or searching through case files (step 250), or adding new cases to the database (step 210). In addition to these two processes, some of the users will be accessing the editor routine (step 220), working with teaching files (step 240), or other specialized review processes such as the consultation process of step 230. The system may also be designed to mask those processes, or options within a given process, for which a user does not have sufficient privileges.

When a user wants to create a new case, he or she begins by selecting the new-case creation process (step 210). In a preferred system, this data entry process is streamlined, and the user is only presented with data entry options tailored to the type of information he or she is most likely to enter. This may be accomplished by first prompting the user to select the type of data that she wishes to enter. Thus, while users may generally be encouraged to enter as much data as they feel appropriate, if all they want to enter for a particular case is image/caption data, they may conveniently accomplish this by clicking or selecting, or using other interactive means, an image/caption entry, following which the system returns a more tailored data-entry interface.

The system may also be designed to be responsive to pre-stored information concerning the registered user. In that case, a narrower set of options and data-entry interfaces tailored to the medical practice field of the user may be presented. In doing so, the system streamlines the process as much as possible for doctors of a given specialty. This has the benefit of not only saving the doctors time in the data-entry stage, but by narrowing the options to those relevant to their specialty and removing confusing clutter from the entry process, an improved quality can also be achieved for the data being entered.

Figure 3:
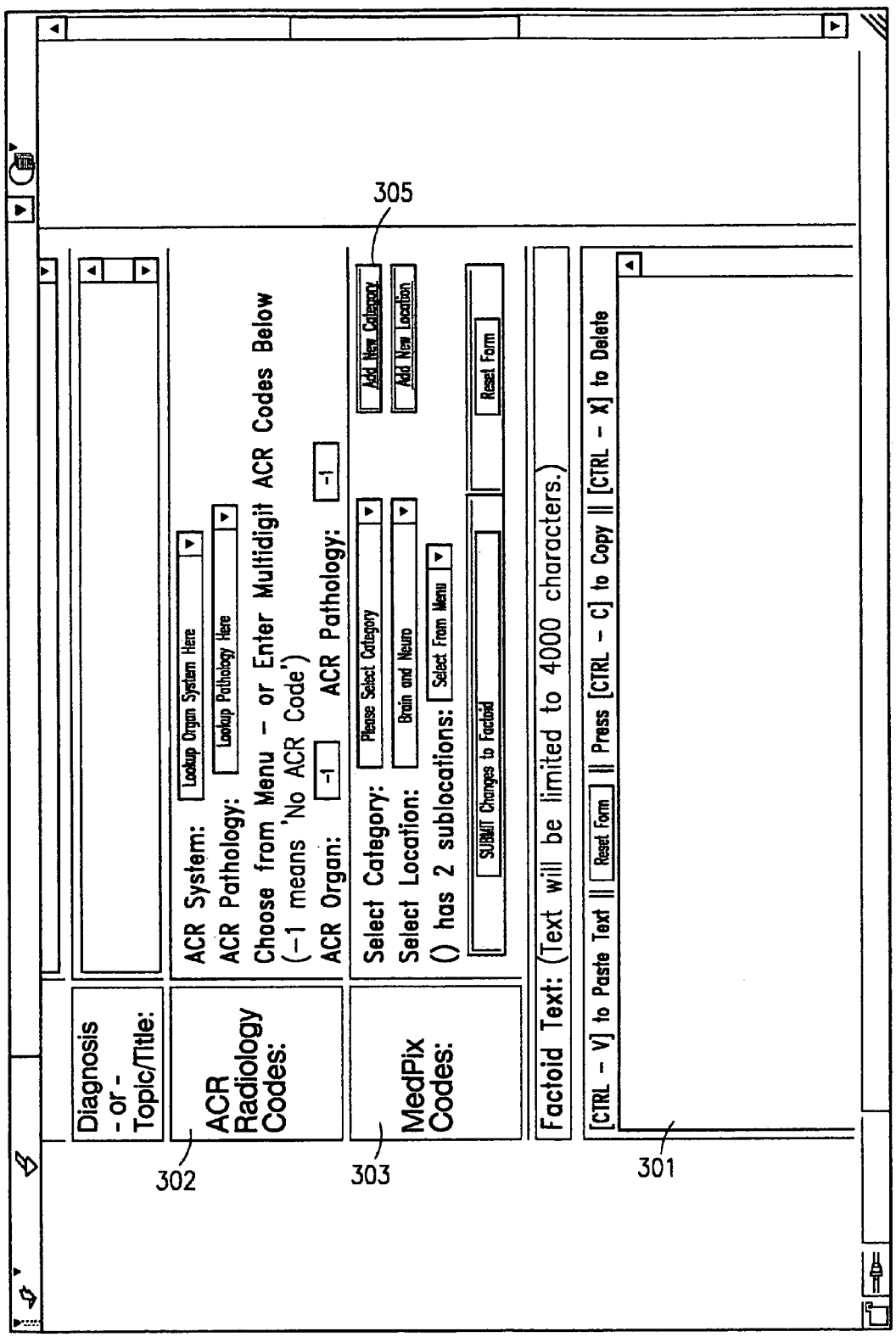

A current implementation for use in capturing case data is illustrated in FIG. 3. This figure shows a Web browser-enabled data entry interface, via which any user having a web browser can communicate data with the database. In the illustrated case, a user begins with selection of a factoid entry option. In response, the system returns appropriate HTML pages as data-entry interfaces. The entry of text describing the disease or condition information is thus possible, for example, via Text Entry Box 301.

A variety of other data-capture tools may also be presented. If the user is a radiologist, a pull-down menu may be used to help them rapidly select appropriate ACR radiology codes. By hierarchically linking the data available for the pull-down menus, a user can rapidly progress from general systems down to the unique name or code identifying the particular condition or disease. Other well-known codes, such as the ICD codes, may be used as appropriate. A user community may also find it convenient to implement a more generic coding system, such as the MedPix codes block that is illustrated in connection with FIG. 3. In developing such coding schemes, it is useful to allow certain users to have privileges to add new entries to the pull-down lists, such as the Add New Category box 305 for MedPix codes 303. Thus, through interaction with the broader user community, a more tailored hierarchical coding structure can be rapidly developed for that community.

Any other desirable information relating to the disease or condition should also be prompted for user input at this point. Such information could include a descriptive title for the factoid, the narrative entry described above, keywords associated with the information being entered, system and location information (organ, body part), or other category information (e.g., type of disease). In a more robust system, the fixed-entry items such as the pull-down menus and codes will also be processed against appropriate expert rules, so that a user can be prompted during the data-entry stage to change entries that appear to be in conflict or otherwise trigger a rule violation. Finally, once a user is finished entering the factoid information, she need only click on the Submit button for the data to be forwarded for entry to the multimedia database management system.

If all that the user wanted to enter was factoid information, the user could exit the system at this point. However, for a complete case the user would want to proceed and enter the patient and image information also. For a typical user this can be conveniently accomplished by including all the appropriate entry fields and prompts on the same new case-creation screen. The user would then proceed to enter image information (step 214) by scrolling down and selecting or inputting appropriate caption information, and uploading an image file from their location to the database. To simplify the user's process of inputting this information a wide variety of media formats may be accepted. However, the multimedia database system preferably includes appropriate image converters for resizing or formatting the image into one of a selected group of formats for consistency. It is also desirable for the system to have the capability of automatically generating thumbnail images at this point, making subsequent display and browsing more convenient for users. All of this information would typically be stored in the same record in the image table, and appropriately related to the other tables of the multimedia database (e.g., the factoid and patient tables).

Finally, a user can also input relevant patient and clinical data at the same time the factoid and image data are entered. This information could include, e.g., demographic information, history, other treatments, and the like. To the extent private or other sensitive information is added, the user may also be granted the option of setting higher access restrictions regarding who can view the information (step 216). Once all the desired information has been added, the user submits it for appropriate processing and posting.

While this new file creation process has been described in connection with a browser-enabled system, those of skill in the art will appreciate that any one of a variety of data-entry systems may be utilized. Thus, proprietary templates or non-browser enabled access screens can be used, e.g., as may be found in connection with many database systems. But, in addition to systems oriented around keyboards and mice, appropriately configured touch-screen systems (like PDAs), or even voice-recognition enabled systems may be used as part of the data-entry interface to the user. Moreover, while the multimedia medical database has been particularly described in connection with the storage and use of image data, a skilled artisan will readily appreciate how the system may be used with any appropriate form of non-text data. For example, audio information, audio-visual information, or other captured electromagnetic information from medical instrumentation, or the like, may be stored as part of the captioned image (multimedia) table record, and accessed by users with appropriately configured interfaces. Accordingly, in the context of the present application, the term 'image' should be read as representative of all non-textual multimedia information, and not just restrictively in the sense of non-alphanumeric visual representations or objects.

In a preferred system, each image/caption record will have both mandatory and optional descriptors. The mandatory descriptors should be chosen so as to facilitate subsequent viewing and data mining, and can vary by medical specialty. Some useful types of descriptors include: the image plane (e.g., coronal, sagittal, etc.), image type (e.g., MR, CT, surgical, clinical, etc.), ACR code, MedPix (or other proprietary) code, image source and creation information, copyright/privacy restrictions, and the like. During the case creation process, this image/caption information is relationally cross-linked to the factoid and/or patient profile table information, to the extent such additional information is entered for a given case. In addition to the images that are stored as part of the record, the system may also be implemented so as to archive a copy of each image as originally uploaded by the author (including the original file name if desired).

Similarly to the process with image/caption tables, mandatory and optional fields may also be employed with the factoid and patient tables. Examples of some of the mandatory fields that could be employed with a factoid include: the title, an ACR code, the location/organ system, the disease category, and the factoid text. If the user has started to create a case, but does not have all the mandatory information or for some other reason is not yet prepared to submit a case, the system may also include a temporary storage feature by which an author can save a partially completed case and finish its completion at a later time.

Once a new case has been entered, it is automatically placed in an electronic submissions bin, along with other new cases, for editorial review. While this editorial process may not be required in all implementations, it does help enforce a higher standard of quality and integrity for the data being made available to the practitioners using the system. This editorial review process typically begins by an automated assignment of a new case file to an editor who is authorized to review that type of case. The editorial selection can be based on any convenient category, such as the MedPix or ACR codes, organ/location information, patient or image type, etc. In lieu of assigning specific editors, all or a portion of the new cases may be available for anyone within a group of editors to select. The type of assignment process chosen is largely a matter of convenience for the editors, balanced against the need for timely review of the new submissions being held or otherwise tagged for restricted access pending editorial review.

The next step in the editorial review process (step 220) may commence at any time an assigned editor is connected to the system. The editor can be prompted via any appropriate push technology (like e-mail, screen alerts, pages sent by the review module) that new submissions are waiting for his review, or the editor can initiate a review via a button or other appropriate prompt to access a review menu. Once the review process has begun and a particular file is open, the editor proceeds to review it for accuracy, and is able to modify most of the file information as needed (steps 222–226). After his review is over, the editor approves and closes the file, at which point the system automatically updates the file and makes it available to authorized system users (step 228).

Any time a file is altered outside of the editorial review process, it is preferable to have it automatically returned to the electronic submissions bin for further review. On the other hand, in appropriate circumstances the editorial review process may be modified or bypassed. For example, it may be desirable to permit submissions by specially qualified editors, or even peer-level systems administrators performing batch uploads of pre-qualified information, so cases can be immediately released without the delay of the typical editorial review process.

Another circumstance in which case information may be made available to other users prior to an editorial review is illustrated in connection with steps 230–236. These steps illustrate a consultation process by which the multimedia medical database can be used for live or contemporaneous consultations. When entering this mode, the physician creating the new case can be given the option to tag it for immediate review by consulting physicians. This process may be facilitated by the system allowing the case author to grant limited review and/or edit privileges to other system users designated by the author. One way of accomplishing this is allowing the author to solicit interested physicians, for example by e-mail, browser, or other suitable alert. While the author can generate e-mails on his own to physicians with whom he has an established relationship, the multimedia database system may optionally provide an automated solicitation service (by e-mail, web browser alerts, or the like) to other registered users of the system.

Once another physician has responded to the request for consult services, she need only log on to the system and retrieve the designated case for which the author has extended consult privileges. Alternatively, the first physician could provide a password or other access criteria (including but not limited to a name, certificate, or verified id) for the consulting physician to use when accessing the file.

At this point, both physicians may contemporaneously (i.e., within minutes or hours, if not seconds, of each other) or even simultaneously review the same case information. If desirable, the physicians can enter a chat (voice, text, or graphics) mode, enter comments on the file, or otherwise edit the data. An appropriately configured system (e.g., with Internet telephony capabilities) may even allow voice or multimedia conferencing between the physicians while they are at their computer or network terminals (step 234). Special diagnostic, prescriptive, or other information can be stored in the private patient table fields (step 235). As part of the consultation process, one or both physicians may also conduct simultaneous searches within the multimedia medical database for pertinent information relating to the consult. Finally, once the consult is over, the author may select to submit the case file for further processing and posting, as described above in connection with a typical new case creation process (step 236). Steps 240–247 illustrate yet another interactive process for use with the multimedia medical database. This process is particularly advantageous for use in connection with interactive presentations or teaching events. The author begins by initiating a case builder for use with the presentation (step 240). This may be similar to the process for building a new case, as is illustrated by FIG. 4. If available and convenient, pre-existing case information can be reused and edited; otherwise, an entirely new case may be built (step 241). If pre-selected data is used, the author can edit this data within the context of the teaching file to better tailor it for its teaching purposes. The system also, preferably, provides the author with a simplified process by which the selection, modification, special questions, special presentation features, and results are captured. Thus, a user-friendly template can be provided for users who are not otherwise familiar with, e.g., HTML document authoring. This template would be prepared in a manner to prompt a user to input desired text and image information, presentation information, user information and the like, and an application for taking the user inputs together with pre-defined information (such as formatting, privileges, etc.) to create an end-product. This helps expedite the process of inserting the instructions and questions wanted for presentation to the audience/students, determining any special ordering in which the information is presented, and providing the links, e.g., to secure file(s) for storage for the interactive responses. By way of illustration, in a typical case a teaching physician may start by selecting a known case having interesting factoid and clinical information, along with selected images. If the goal of the presentation is to test knowledge relating to the images, the author would modify or delete unnecessary clinical information, adjust the factoid information as appropriate, and add additional images that are not accurately related to the described factoid. This file is then stored (step 242) for later retrieval by the student (step 245). When reviewing the file, the student would be presented with the appropriate instructions, factoid, clinical, and image information pre-selected by the teaching physician. As the student selects the image that she thinks is correct, the result is captured in a report file/table. The correct answer is also displayed at that time (step 246–247).

While the teaching case builder has been discussed in connection with a simple test involving the selection of correct images, those skilled in the art will readily appreciate its versatility for use in testing almost any information related to a case. Thus, for example, the author could just as easily have presented complete image information, but omitted certain clinical or factoid information and asked the student to select or fill-in what she believes is the correct information. Further, where a series of cases have been designed into a module, an expert system can be advantageously used—such as systems which those skilled in the art will readily recognize as being used in connection with edutainment software programs—to select subsequent cases based upon the student's responses to earlier ones. Thus, if the student has correctly answered one or more of a class of questions, the program could automatically select a subclass or altogether different class (e.g., making the testing harder, or moving onto other subject matter areas). Further, its utility beyond simple testing should also be apparent. It can, for example, be readily adapted to facilitate interactive continuing education to medical professionals, with the answers being provided to the professional taking the teaching module (i.e., sequence of cases) and, if desirable, to other interested entities (certifying boards, local hospitals, payor entities and the like).

Turning now to steps 250–268, a process for viewing stored cases is illustrated. This process begins at step 250, with the registered user selecting the View or Search option. The user can start this either at his initial logon, or can alternatively link to this view mode by selecting an appropriate button available within one of the other system windows. FIG. 5 illustrates one possible search entry window (step 255). As a matter of convenience to the user, a selection of possible search categories is presented at the top of the page, FIG. 5A. FIGS. 5B and 5C illustrate a range of options available when searching by images or factoid information. Because of the relational nature of the case information stored in the tables of the multimedia medical database, a variety of search criteria from one or more of the available table fields can be used in developing a search as broad or as narrow as the user desires. Thus, a user may search for all cases in which the words brain and tumor appear in the image captions, or may further limit it by topical or text information from the factoid tables. More advanced users can design their own search criteria by, e.g., writing their own Boolean search script.

Figure 6:
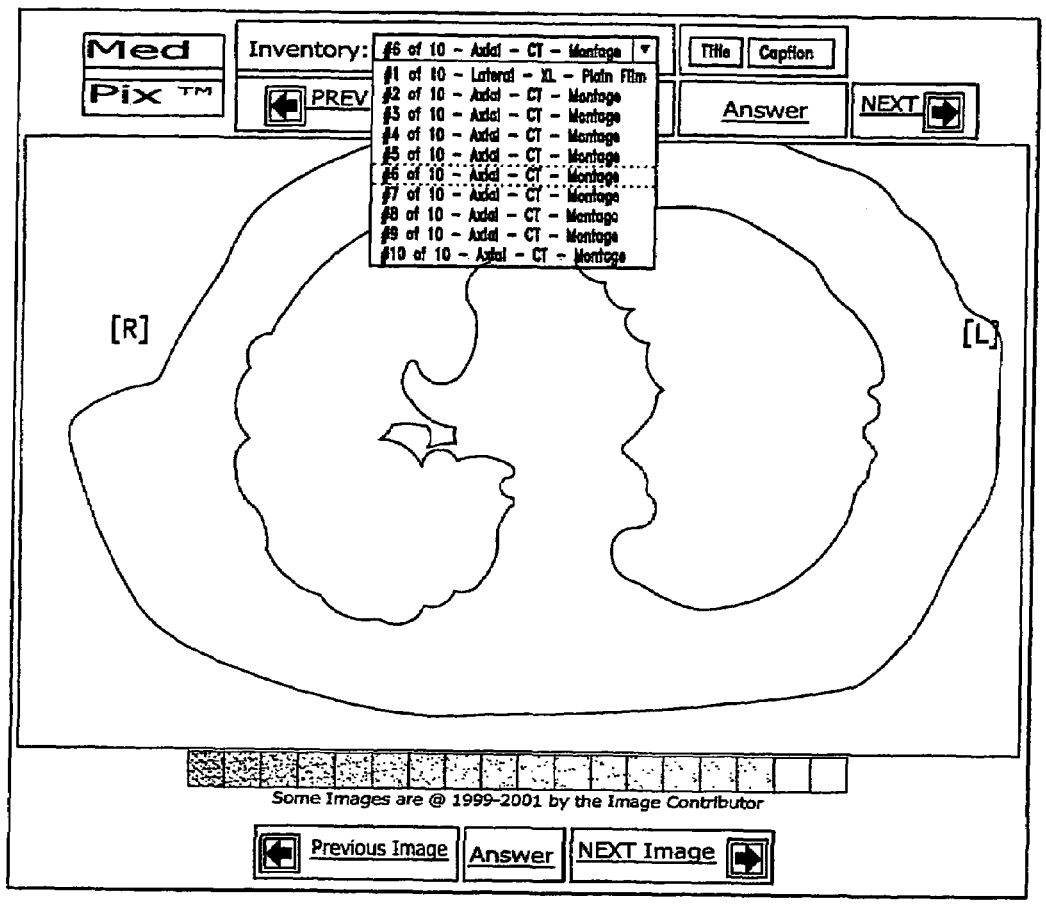
Figure 7B:
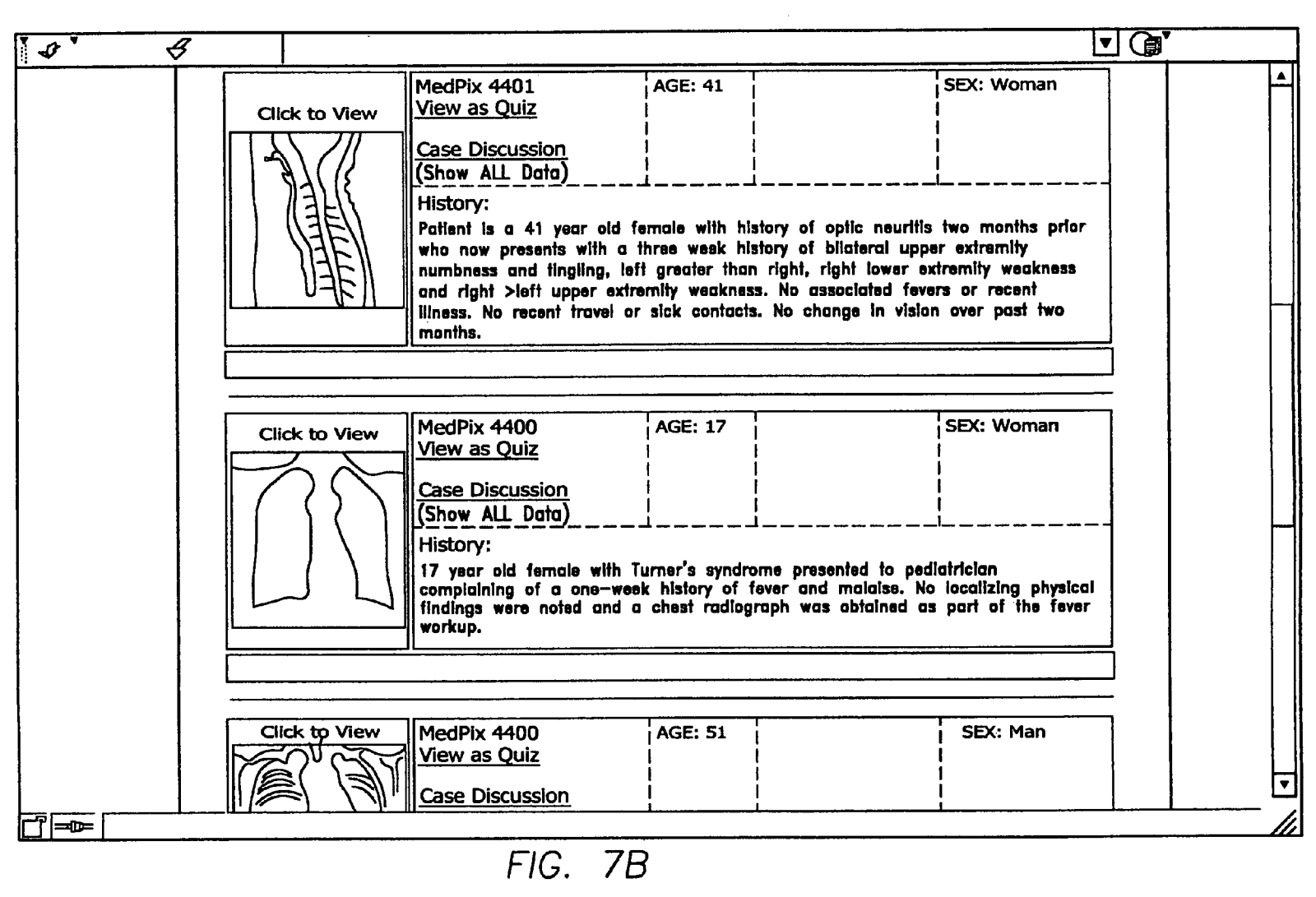
Figure 8A:
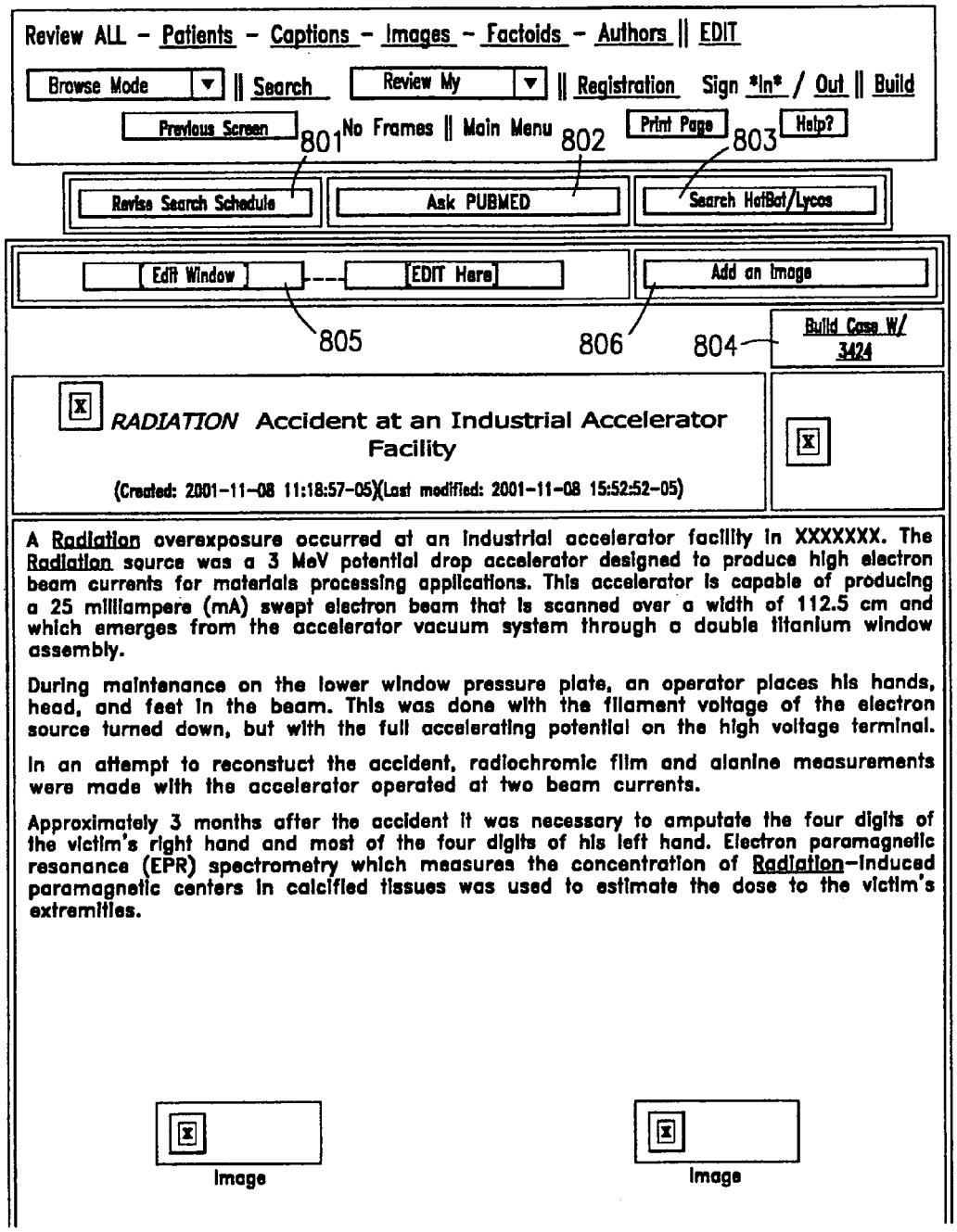
Figure 9B:
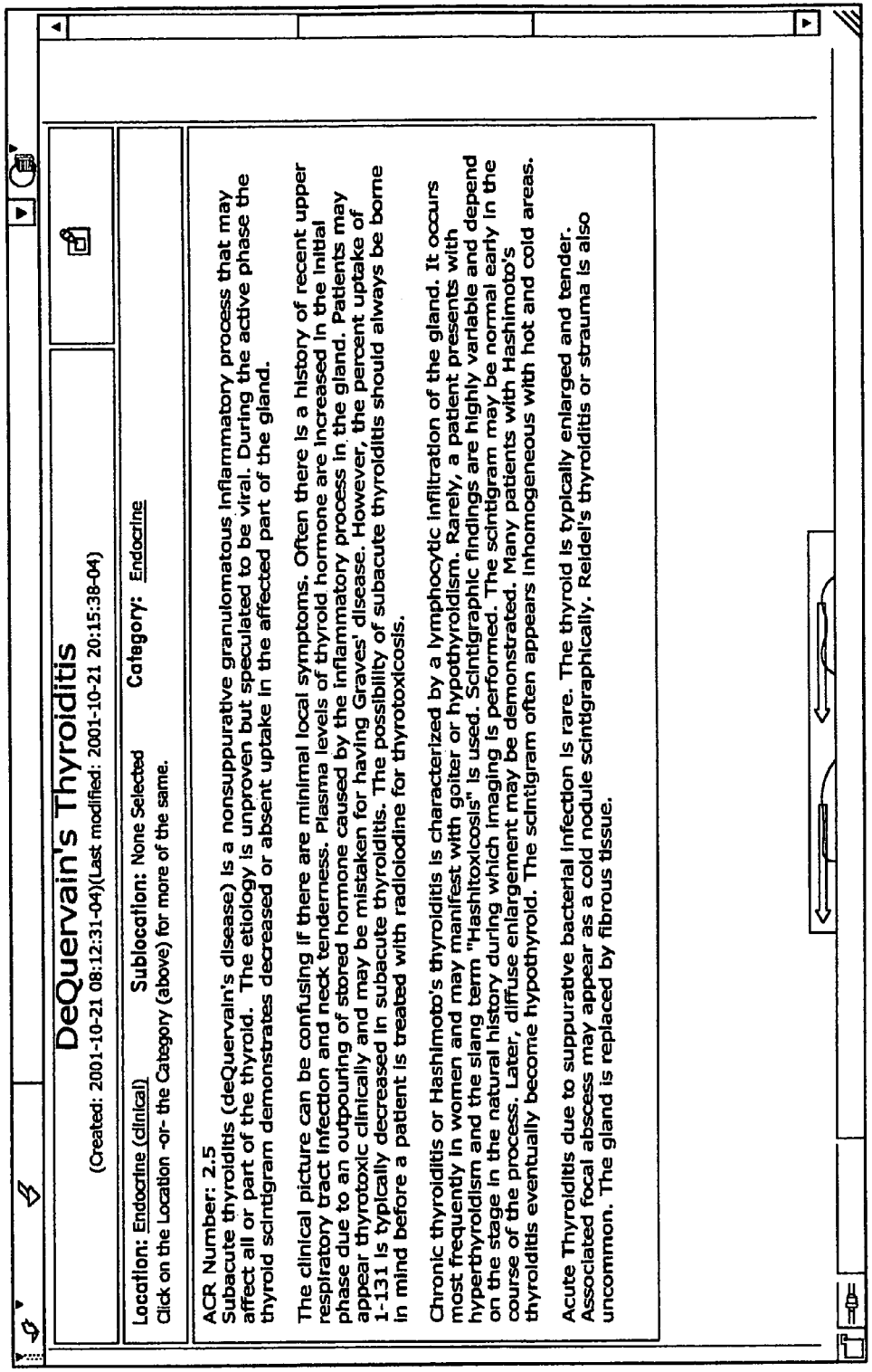
Figure 9C:
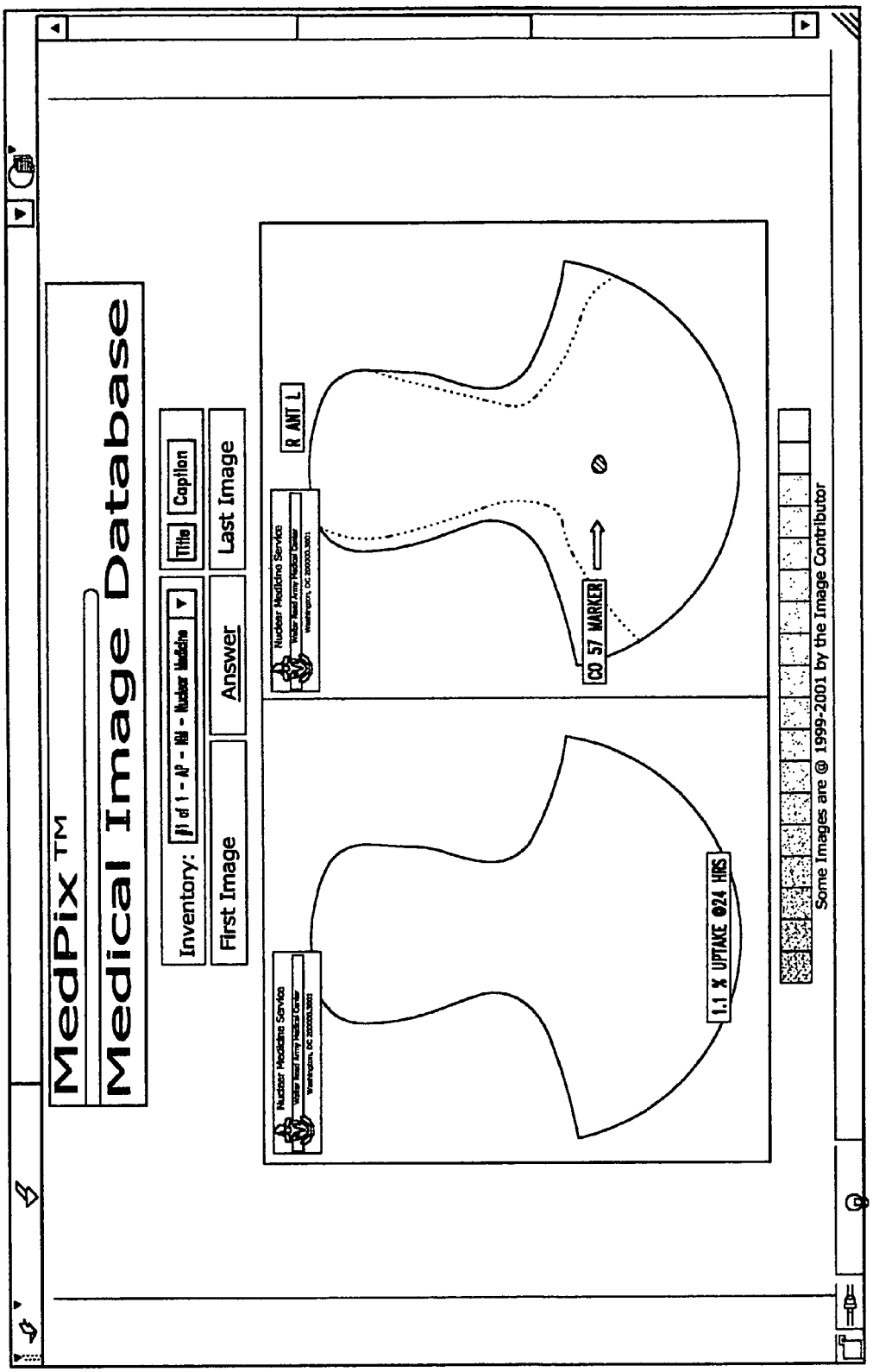

Once a query has been entered, the user next selects files for viewing from the retrieved results (steps 260–265). FIG. 6 illustrates one implementation for viewing returned image information via a case navigator. Tools such as buttons for previous and next images, and pull-down menus for moving between images, may be used to assist the doctor in moving between the retrieved files. FIG. 7 illustrates an alternative implementation in which conditional information like codes and non-private patient information are displayed for rapid browsing of the returned results, along with appropriate links to additional information. FIGS. 8A and 8B illustrate a returned case file in a format that includes image and factoid information. The buttons on this page also illustrate the versatility that can be added via a multimedia medical database system. For example, a user can choose to continue his search through links back to internal search interfaces, or through links out to external search facilities (buttons 801–803). A user interested in building another case can use the link via button 804 to start building such a case. A user with appropriate authorization can edit the window or add images via buttons 805 and 806. Reviews or comments can also be added via button 807. FIG. 9 illustrates yet another approach towards the return of search results. In this case, FIG. 9A shows a search performed around location information (the endocrine/thyroid). In response to a user's view selection (or edit selection, if authorized), a selected factoid is returned, as shown by FIG. 9B. In further response to the selection by the user of an image thumbnail 902, the image of FIG. 9C is then displayed.

Figure 10A:
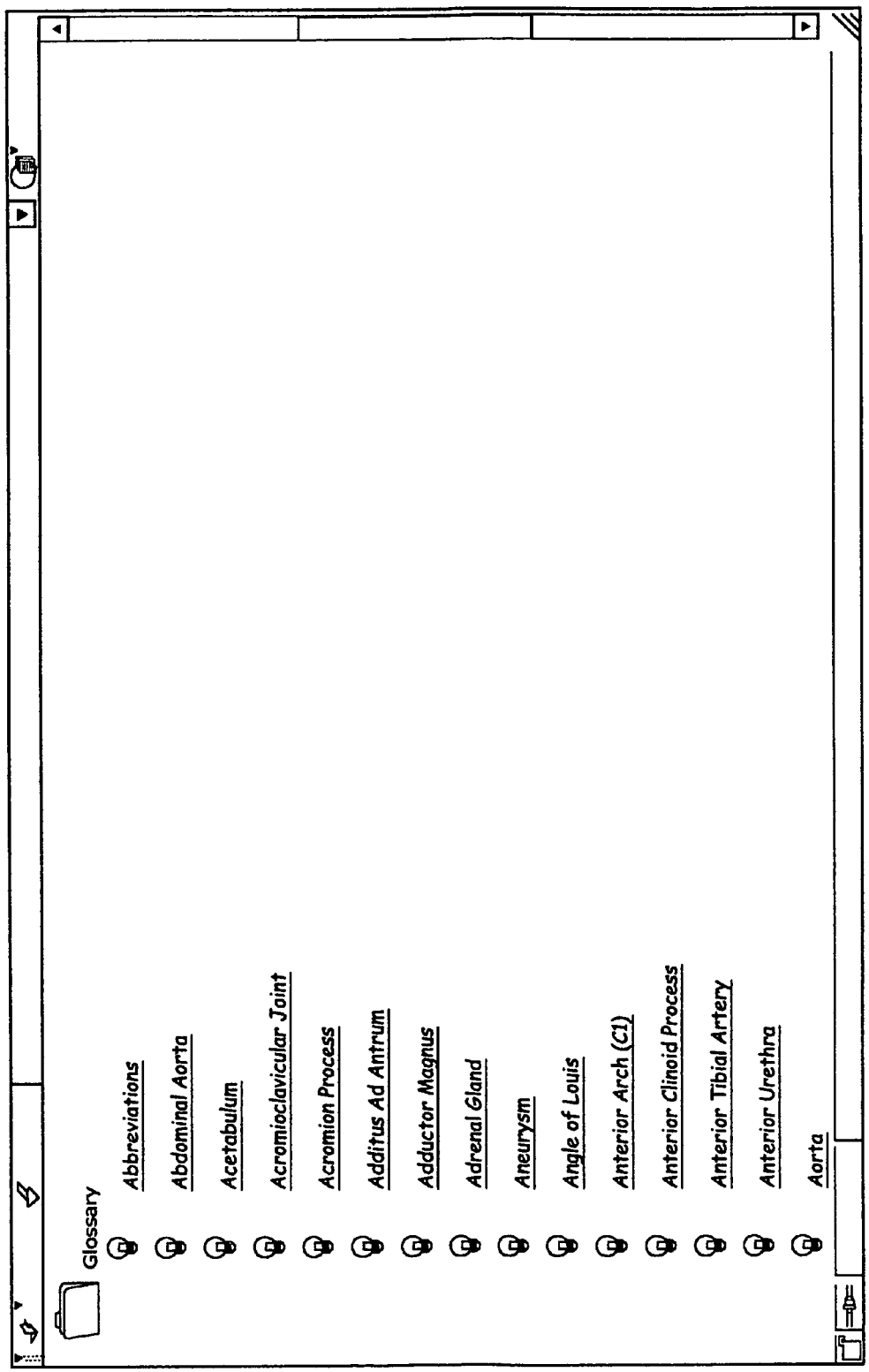
FIGS. 10A–10B illustrate another approach to browsing, starting with a glossary of key terms (FIG. 10A), and returned medical information for browsing in response to a term selection (FIG. 10B)
Figure 10B:

As FIGS. 5 through 9 illustrate, a user can rapidly search and navigate through a large database of images and information using the present invention. Several implementations for how such a search can be done within a browser-enabled environment have been illustrated, but one skilled in the art will readily understand how to more broadly or narrowly enable searches based on the preferences of the user communities involved. One such additional approach is illustrated in connection with FIGS. 10 and 11, which illustrate the browse modes of step 252 and 254. Starting with FIG. 10A, a glossary of keywords and titles can be built. This information is preferably captured via the use of pull-down menus or other fixed lists presented at the time case files are entered. Using such a glossary, a user can scroll down and select the glossary term of interest, which in the illustrated case of FIG. 10B is the adrenal gland. While a glossary file is likely to be more generic in scope, it will contain links to related information such as the illustrated location code (which can be used in further searching) and links to external URLs. One can also use the Case Builder button in the process of building a new case.

FIG. 11 illustrates yet a different approach to browsing. Starting with FIG. 11A, a listing of potential criteria (anatomic locations) for selection by the user is displayed in response to the user's selection of browsing factoids by anatomic location. Using any of the well-known processes for expanding HTML-based lists, FIG. 11B illustrates how the multi-system location entry has been expanded to display possible selections within that category. After a user selects the Angiogenesis button, a listing of the angiogenesis factoids is returned. In the illustrated case, where there is only one factoid, a single case file may be returned, such as is further shown in FIGS. 11C and 11D. Alternatively, a listing of files substantially matching the search/browse criteria may be returned containing summary information (such as a title or caption), from which the user may then select an individual case file. Once the individual file is returned, the user is able to view and make authorized edits, and link to other pages or sites, as he or she might from any typical displayed case screen.

In conclusion, what has been disclosed is a new medical multimedia database system. The database includes relationally linked disease or factoid information, image/caption, and patient/condition tables, respectively, which in operation store disease/factoid data, image/caption (or other multimedia) data, and patient/condition data, respectively. Because of the relational linkages, part or all of the information from any given case, which is stored in related records in the different tables, can be returned in a variety of formats, depending on factors such as the context and privileges of the user. The methods and apparatus of this system can be implemented to allow simple entry and searching for relative novices, but also be scaled upwards to usably store vast amounts of information and allow for complex searches and re-uses of case information. Some of the somewhat more complex applications have been touched on in the examples of interactive learning and remote consultation described above.

In the current implementation of this system, an apparatus and method for a medical multimedia database system comprises (a) a disease information table which is operable to store plural disease factoid files; (b) an image table which is operable to store plural image files each comprising at least image and image caption information; (c) a patient data table which is operable to store plural patient files each comprising one or more patient and clinical data items; (d) where the factoid, image and patient tables are operably coupled such that related factoids, images, and patient data are relationally linked to each other as a case files. This relational coupling can take any desirable form, e.g., from a simple relating of one image record to one factoid record to one patient record, to a relating of one factoid record to a multitude of image records, to a complex matrix of cross-related image, factoid and patient records. This system further comprises: remote user input of case files; a verification process limiting access to new case files until approved by peer reviewers; a peer review process whereby users with comment privileges can append comment data to a case file; enhanced case files, comprising simple and complex relationships, including a linking of related case files by specified components (e.g., the same patient file linked to multiple factoid/image files); interactive training systems for selectively displaying case file information, further linked to a training table including expert training file information interactively responsive to user-selected inputs, and also linked to a training table for storing student results; a consultative program system for selectively presenting case file information for contemporaneous or real-time review of multimedia medical case files; and privacy and access limitation features. The privacy and access features are preferably implemented via an access control module; the search and browse features are preferably implemented via a search module of the DBMS 111; and the learning (file builder and presentation), consultation, expert, and reviewer features are preferably implemented via learning file builder, presentation, consultation, expert and review modules, respectively. These modules may be separate and even remote programs, or integrated (partially or wholly) together with the medical multimedia database program, depending on the design choices of those skilled in the art implementing the system.

It is believed that the operation and construction of the present invention will be apparent from the foregoing description. While the method, apparatus and system shown and described has been characterized as being preferred, it will be readily apparent that various changes and modifications could be made therein without departing from the scope of the invention, and that the invention is not limited to these embodiments. For example, those skilled in the art will appreciate how each of the elements of the aforementioned embodiments may be utilized alone or in combination with elements of the other embodiments. These and further modifications may be made by those skilled in the art, particularly in light of the foregoing teachings, without departing from the scope of the invention.

We claim:

1. A medical image database system having plural tables comprising:
   a. a disease information table, operable to store plural disease factoid files;
   b. an image table, operable to store plural image files each comprising at least one of an image and image caption information;
   c. a patient data table, operable to store plural patient files each comprising at least one of patient information and clinical information;
   wherein the disease information, image, and patient data tables are operably coupled such that a related first factoid file, a first image file and a first patient file are relationally linked to each other as a first case file;
   d. a new case file creation module, operably coupled to the tables for adding a new case file in response to a user input;
   e. an educational file builder module, operably coupled to the tables and new case file creation module, and operable to (i) provide selection criteria to the user for designing an educational file based in part on the new case file; and (ii) processing selection criterion received from the user, allowing the user to add at least one of inaccurate information to or withhold omitted information from the educational file; specifying an answer prompt, a correct answer to the answer prompt, so as to built and store the educational file; and
   f. a presentation module, operable to (i) present the educational file to a further user; (ii) capturing an answer input in response to the answer prompt; and (iii) returning the correct answer to the further user.

2. The system of claim 1, wherein the new case creation module is further operably coupled to the tables for adding a new case file including factoid, image and patient data in response to a user input, the system further comprising:
   a security module, operable to determine a user's access privileges to the tables; and
   a new file creation module, operably coupled to the tables for adding a new case file including factoid, image and patient data in response to a user input; and
   a review module, operably coupled to the tables and the security module, and operable to provide new case files to at least one reviewer to review the content of the new case file, to receive one or more modifications from the reviewer and apply said modifications to the new case file, and to receive an approval indication from the reviewer and operate together with the security module to change one or more access privileges of the new case file.

3. The system of claim 1, wherein the new case creation module is further operably coupled to the tables for adding a new patient case file including factoid, image and patient data in response to a first user's inputs, the inputs also including a criterion for access to the patient case file by additional users, the system further comprising:
   a security module, operable to determine a user's access privileges to the tables; and
   a new file creation module, operably coupled to the tables for adding a new patient case file including factoid, image and patient data in response to a first user's inputs, the inputs also including a criterion for access to the patient case file by additional users; and
   a review module, operably coupled to the tables and the security module, and operable to provide the new patient case file to at least one further user of the additional users to review the content of the patient case file, to receive one or more modifications from said further user and apply said modifications to the patient case file.

4. The system of claim 3, further comprising:
   a consultation module, operably coupled to the review module and operable to provide contemporaneous access to the new patient case file to the first user and said further user and contemporaneous communications between the first user and said further user relating to the new patient case file.

5. The system of claim 4, further comprising:
   a search module, operably coupled to the tables and operable to return to the further user, substantially contemporaneous with said access to the consultation module, case file information from at least one of the disease information, image, and patient data tables, in response to search criteria related to the new patient case file.

6. The system of claim 5, wherein the review module further comprises logic to provide the new patient case file to a reviewer to review the content of the new patient case file, to receive modifications from the reviewer and apply said modifications to the new case file, and to receive an approval indication from the reviewer and operate together with the security module to change one or more access privileges of the new patient case file.

7. The system of claim 1, wherein the educational file builder module further comprises logic for creating a sequence of related educational files, and the presentation module further comprises logic for presenting at least part of said sequence of related educational files.

8. The system of claim 7, further comprising:
   g. an expert module, operably coupled to the tables and presentation module, and operable to (i) determining an accuracy level of answer inputs for said at least part of said sequence of related educational files, and (ii) determining a next educational file to present to the further user based in part on said determined accuracy level.

9. The system of claim 7, wherein the further user is a medical student and the presentation module further comprises logic for capturing answer inputs by the medical student for each of the sequence of related educational files and storing a representation of the captured answer inputs for subsequent use by an educator.

10. A medical image database system comprising:
    a. plural tables, comprising (i) a disease information table, operable to store plural disease factoid files, (ii) an image table, operable to store plural image files each comprising at least one of an image and image caption information, and (iii) a patient data table, operable to store plural patient files each comprising at least one of patient information and clinical information; wherein the disease information, image, and patient data tables are operably coupled such that a related first factoid file, a first image file and a first patient file are relationally linked to each other as a first case file;
    b. a new case file creation module, operably coupled to the tables for adding a new case file in response to a user input;
    c. an educational file builder module, operably coupled to the tables and new case file creation module, and operable to (i) provide selection criteria to the user for designing an educational file based in part on the new case file; and (ii) processing selection criterion received from the user, allowing the user to add at least one of inaccurate information to or withhold omitted information from the educational file; specifying an answer prompt, a correct answer to the answer prompt, so as to built and store the educational file; and d. a presentation module, operable to (i) present the educational file to a further user; (ii) capturing an answer input in response to the answer prompt; and (iii) returning the correct answer to the further user;

wherein the educational file builder module further comprises logic for creating a sequence of related educational files, and the presentation module further comprises logic for presenting at least part of said sequence of related educational files; and wherein the further user is a medical student and the presentation module further comprises logic for capturing answer inputs by the medical student for each of the sequence of related educational files and storing a representation of the captured answer inputs for subsequent use by an educator.

11. A method for providing remotely accessible medical image database information via a medical image database having plural tables, comprising:

a. storing plural disease factoid files in a disease information table;

b. storing plural image files each comprising at least one of an image and image caption information in an image table;

c. storing plural patient files each comprising at least one of patient information and clinical information in a patient data table;

d. operably coupling the disease information, image, and patient data tables such that an at least one factoid file, at least one image file and at least one patient file are relationally linked to each other as a first case file;

e. adding a new case file in response to a user input;

f. creating an educational file by (i) providing selection criteria to the user for designing an educational file based in part on the new case file; and (ii) processing selection criterion received from the user, allowing the user to add at least one of inaccurate information to or withhold omitted information from the educational file; specifying an answer prompt, a correct answer to the answer prompt, so as to built and store the educational file; and g. facilitating learning by a further user by (i) presenting the education file to a further user; (ii) capturing an answer input in response to the answer prompt; and (iii) providing the correct answer to the further user in response to an incorrect answer input.

12. The method of claim 11, wherein step f further comprises creating a sequence of related educational files, and step g further comprises presenting at least part of said sequence of related educational files and capturing each answer input provided in response thereto.

13. The method of claim 12, wherein step g further comprises (i) determining an accuracy level of said answer inputs, and (ii) determining a next educational file to present to the further user based in part on said determined accuracy level.

14. The method of claim 12, wherein the further user is a medical student and step g further comprises capturing answer inputs by the medical student for each of the sequence of related educational files and storing a representation of the captured answer inputs for subsequent use by an educator.

15. A method of facilitating learning by medical professionals regardless of distance using a medical image database having plural tables, comprising:

a. storing plural disease factoid files in a disease information table;

b. storing plural image files each comprising at least one of an image and image caption information in an image table;

c. storing plural patient files each comprising at least one of patient information and clinical information in a patient data table;

d. operably coupling the disease information, image, and patient data tables such that an at least one factoid file, at least one image file and at least one patient file are relationally linked to each other as a first case file;

e. adding a new case file in response to a user input;

f. creating an educational file by (i) providing selection criteria to the user for designing an educational file based in part on the new case file; and (ii) processing selection criterion received from the user, allowing the user to add at least one of inaccurate information to or withhold omitted information from the educational file; specifying an answer prompt, a correct answer to the answer prompt, so as to built and store the educational file; and g. facilitating learning by a further user by subsequently (i) presenting the education file to the further user; (ii) capturing an answer input in response to the answer prompt; and (iii) providing the correct answer to the further user in response to an incorrect answer input.

16. The method of claim 15, wherein step f further comprises creating a sequence of related educational files, and step g further comprises presenting at least part of said sequence of related educational files and capturing each answer input provided in response thereto.

17. The method of claim 15, wherein step g further comprises (i) determining an accuracy level of said answer inputs, and (ii) determining a next educational file to present to the further user based in part on said determined accuracy level.

18. The method of claim 15, wherein the further user is a medical student and step g further comprises capturing answer inputs by the medical student for each of the sequence of related educational files and storing a representation of the captured answer inputs for subsequent use by an educator.

* * * * *